United States Patent
Jang et al.

(10) Patent No.: US 10,196,511 B2
(45) Date of Patent: Feb. 5, 2019

(54) THERMOPLASTIC RESIN COMPOSITION AND MOLDED PRODUCT ARTICLE INCLUDING THE SAME

(71) Applicant: LG CHEM, LTD., Seoul (KR)

(72) Inventors: Seok Goo Jang, Daejeon (KR); Jeong Su Choi, Daejeon (KR); Keun Hoon Yoo, Daejeon (KR); Won Seok Lee, Daejeon (KR); Roo Da Lee, Daejeon (KR); Sang Hoo Park, Daejeon (KR); Ho Hoon Kim, Daejeon (KR); Hyung Seop Shim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/545,247

(22) PCT Filed: Dec. 1, 2016

(86) PCT No.: PCT/KR2016/014033
§ 371 (c)(1),
(2) Date: Jul. 20, 2017

(87) PCT Pub. No.: WO2017/099419
PCT Pub. Date: Jun. 15, 2017

(65) Prior Publication Data
US 2018/0002521 A1  Jan. 4, 2018

(30) Foreign Application Priority Data
Dec. 11, 2015  (KR) .......................... 10-2015-0176656

(51) Int. Cl.
| | | |
|---|---|---|
| *C08L 33/20* | (2006.01) | |
| *C08L 33/08* | (2006.01) | |
| *C08L 33/10* | (2006.01) | |
| *C08L 51/04* | (2006.01) | |
| *A01N 59/16* | (2006.01) | |
| *C08L 33/12* | (2006.01) | |
| *C08J 5/00* | (2006.01) | |
| *C08L 51/06* | (2006.01) | |

(52) U.S. Cl.
CPC .............. *C08L 33/12* (2013.01); *A01N 59/16* (2013.01); *C08J 5/00* (2013.01); *C08L 33/08* (2013.01); *C08L 33/20* (2013.01); *C08L 51/06* (2013.01); *C08L 2201/10* (2013.01)

(58) Field of Classification Search
None
See application file for complete search history.

(56) References Cited

U.S. PATENT DOCUMENTS

| | | | | |
|---|---|---|---|---|
| 2009/0088309 A1* | 4/2009 | Niida | ..................... | C03C 3/085 501/59 |
| 2014/0017335 A1 | 1/2014 | Dimov et al. | | |
| 2014/0170238 A1* | 6/2014 | Cliff | ........................ | C09D 5/14 424/618 |

FOREIGN PATENT DOCUMENTS

| | | | |
|---|---|---|---|
| CN | 1604941 | A | 4/2005 |
| CN | 103347944 | A | 10/2013 |
| JP | H06-313017 | A | 11/1994 |
| JP | 2001139764 | A | 5/2001 |
| JP | 2005239904 | A | 9/2005 |
| KR | 10-2004-0054985 | A | 6/2004 |
| KR | 10-2006-0032385 | A | 4/2006 |
| KR | 10-2007-0027776 | A | 3/2007 |
| KR | 10-2010-0034458 | A | 4/2010 |
| KR | 20100034458 | A * | 4/2010 |
| KR | 10-2012-0078583 | A | 7/2012 |

OTHER PUBLICATIONS

Esteban-Tejeda et al. (2015) Antibacterial and Antifungal Activity of ZnO Containing Glasses, PloS ONE 10(7). (Year: 2015).*
Machine-generated English translation of KR 20100034458-A.*
International Search Report for International Patent Application No. PCT/KR2016/014033, filed on Dec. 1, 2016.
Chinese Office Action for Chinese Patent Application No. 2016800095719, dated Oct. 23, 2018.

* cited by examiner

*Primary Examiner* — Vu A Nguyen

(57) ABSTRACT

The present invention relates to a thermoplastic resin composition and a molded article including the same. More particularly, the present invention relates to a thermoplastic resin composition including 100 parts by weight of a base resin that includes an acrylic graft copolymer and an acrylic non-graft copolymer; and greater than 0.3 parts by weight and less than 1.2 parts by weight of a zinc-based antimicrobial agent, and a molded article including the same, wherein the zinc-based antimicrobial agent has an average particle diameter of greater than 3 μm to 30 μm. In accordance with the present invention, a thermoplastic resin composition providing superior transparency and excellent initial antimicrobial activity and persistent antimicrobial activity while providing the same mechanical properties as existing resin compositions, and a molded article including the same are provided.

16 Claims, No Drawings

THERMOPLASTIC RESIN COMPOSITION AND MOLDED PRODUCT ARTICLE INCLUDING THE SAME

CROSS-REFERENCE TO RELATED APPLICATION

This application is a U.S. National Stage of International Patent Application No. PCT/KR2016/014033, filed on Dec. 1, 2016, which claims the priority benefit of Korean Patent Application No. 10-2015-0176656, filed on Dec. 11, 2015 in the Korean Intellectual Property Office, the disclosure of which is incorporated herein by reference.

TECHNICAL FIELD

The present invention relates to a thermoplastic resin composition and a molded article including the same. More particularly, the present invention relates to a thermoplastic resin composition providing superior transparency and excellent initial antimicrobial activity and persistent antimicrobial activity while providing the same mechanical properties as existing resin compositions, and a molded article including the same.

BACKGROUND ART

A transparent acrylonitrile-butadiene-styrene resin (hereinafter referred to as "ABS resin") is generally known as a resin having extremely high light transmittance and superior transparency. In addition, since ABS resin has superior impact resistance and processability and excellent mechanical properties, it is being used in electric and electronic fields, OA instrument field, general good field, construction material field, and the like. Particularly, ABS resin is mainly being used in housings for home appliances including air conditioners, vacuum cleaners, washing machines, and the like, housings of OA instruments such as electric and electronic appliances, facsimiles, computers, and telephones, automobile part field, toy part field, leisure article field, interior decoration field, and the like.

Meanwhile, social interest in hygiene and cleanliness has increased in recent years, and thus, a variety of antimicrobial resins have been developed to prevent disease infections caused by fungi or bacteria growing on plastic products and adverse effects thereof on the human body. Generally, antimicrobial resins are prepared by adding an antimicrobial agent to a resin. Particularly, a method of mixing a resin with an organic antimicrobial agent during processing of the resin, a method of mixing a resin with an inorganic antimicrobial agent containing a metal component having antimicrobial activity during processing of the resin, and the like are been known. Here, antibacterial performance and properties are determined according to an antimicrobial agent type and the content thereof. However, when an organic antimicrobial agent is used, an organic antimicrobial agent is easily eluted during a processing process and use thereof. Accordingly, the toxicity of the organic antimicrobial agent per se may damage the human body. In addition, since such an organic antimicrobial agent generally has poor durability, there is a problem such as short persistence of antibacterial performance. On the other hand, when an inorganic antimicrobial agent is used, transparency is decreased due to a difference in refractive index between the inorganic antimicrobial agent and a resin. Alternatively, since an antimicrobial agent is locally coagulated in a resin due to poor compatibility with the resin, antimicrobial activity of the resin is decreased and antimicrobial activity thereof is not reproduced. Accordingly, a large amount of antimicrobial agent is mixed with a resin to increase antimicrobial activity, which causes other problems such as discoloration of the resin, property decrease, and cost increase.

In connection with this, KR2004-0054985 A discloses an antimicrobial resin composition having transparency. However, in preparing the antimicrobial resin composition, inorganic particles having antimicrobial activity are not used. In the case of KR2006-0032385 A, an inorganic silver-based antimicrobial agent is used. Here, since the content of silver is limited to 90% or more, i.e., silver is essentially used at a high concentration, production costs greatly increase.

RELATED ART DOCUMENTS

Patent Documents (Patent Document 1) KR2004-0054985 A
(Patent Document 2) KR2006-0032385 A

DISCLOSURE

Technical Problem

Therefore, the present invention has been made in view of the above problems, and it is one object of the present invention to provide a thermoplastic resin composition providing superior transparency and excellent initial antimicrobial activity and persistent antimicrobial activity while providing the same mechanical properties as existing resin compositions.

It is another object of the present invention to provide a molded article including the thermoplastic resin composition.

The above and other objects can be accomplished by the present disclosure described below.

Technical Solution

In accordance with one aspect of the present invention, provided is a thermoplastic resin composition including 100 parts by weight of a base resin that includes an acrylic graft copolymer and an acrylic non-graft copolymer; and greater than 0.3 parts by weight and less than 1.2 parts by weight of a zinc-based antimicrobial agent, wherein the zinc-based antimicrobial agent has an average particle diameter of greater than 3 µm to 30 µm.

In accordance with another aspect of the present invention, there is provided a molded article including the thermoplastic resin composition.

Advantageous Effects

As apparent from the fore-going, the present invention advantageously provides a thermoplastic resin composition and a molded article including the same. More particularly, the present invention relates to a thermoplastic resin composition providing superior transparency and excellent initial antimicrobial activity and persistent antimicrobial activity while providing the same mechanical properties as existing resin compositions, and a molded article including the same.

BEST MODE

Hereinafter, the present invention is described in detail.

The present inventors confirmed that, when a thermoplastic resin composition having transparency includes a zinc-based antimicrobial agent containing zinc with a particle diameter within a specific range, both initial antimicrobial activity and persistent antimicrobial activity are improved without property decrease, thus completing the present invention.

Hereinafter, the thermoplastic resin composition according to the present invention is described in detail.

The thermoplastic resin composition includes 100 parts by weight of a base resin that includes an acrylic graft copolymer and an acrylic non-graft copolymer; and greater than 0.3 parts by weight and less than 1.2 parts by weight of a zinc-based antimicrobial agent, wherein the zinc-based antimicrobial agent has an average particle diameter of greater than 3 μm to 30 μm.

The acrylic graft copolymer may be prepared, for example, by graft-polymerizing a conjugated diene rubber with one or more selected from the group consisting of a (meth)acrylic acid alkyl ester compound, an aromatic vinyl compound, and a vinyl cyanide compound.

The acrylic graft copolymer may be prepared, for example, by polymerizing 10 to 60% by weight of a conjugated diene rubber, 30 to 70% by weight of a (meth)acrylic acid alkyl ester compound, 5 to 30% by weight of an aromatic vinyl compound, and 1 to 20% by weight of a vinyl cyanide compound.

The conjugated diene rubber refers to a polymer or copolymer prepared by polymerizing a conjugated diene-based compound having a structure wherein a double bond and a single bond are alternately arranged. For example, the conjugated diene rubber may be one or more selected from the group consisting of a butadiene polymer, a butadiene-styrene copolymer, and a butadiene-acrylonitrile copolymer. In addition, the conjugated diene rubber may have, for example, a latex form wherein the conjugated diene rubber is dispersed in water in colloidal state. The conjugated diene rubber may be, for example, a large-diameter conjugated diene rubber having an average particle diameter of 2,500 to 5,000 Å, 2,600 to 5,000 Å, or 2,600 to 4,000 Å. In addition, the conjugated diene rubber may have, for example, a gel content of 60 to 99% by weight, or 70 to 95% by weight and a swelling index of to 35, or 12 to 30. Within these ranges, superior impact strength and processability are exhibited.

The conjugated diene rubber may be included, for example, in an amount of 10 to 60% by weight, or 30 to 60% by weight based on the acrylic graft copolymer. Within this range, superior impact strength, processability, and transparency are provided.

The (meth)acrylic acid alkyl ester compound may be, for example, one or more selected from the group consisting of (meth)acrylic acid methyl ester, (meth)acrylic acid ethyl ester, (meth)acrylic acid propyl ester, (meth)acrylic acid 2-ethylhexyl ester, (meth)acrylic acid decyl ester, and (meth) acrylic acid lauryl ester.

The (meth)acrylic acid alkyl ester compound may be included, for example, in an amount of 30 to 70% by weight, or 30 to 50% by weight based on the acrylic graft copolymer. Within this range, the refractive index of the acrylic graft copolymer is maintained at a proper level with respect to the refractive index of the conjugated diene rubber, whereby superior transparency is provided.

The aromatic vinyl compound may be, for example, one or more selected from the group consisting of styrene, α-methyl styrene, p-methyl styrene, o-methyl styrene, p-ethyl styrene, and vinyl toluene.

The aromatic vinyl compound may be included, for example, in an amount of 5 to 30% by weight, or 5 to 20% by weight based on the acrylic graft copolymer. Within this range, superior processability is exhibited due to excellent fluidity. In addition, the refractive index of the acrylic graft copolymer is maintained at a proper level with respect to the refractive index of the conjugated diene rubber, whereby superior transparency is provided.

The vinyl cyanide compound may be added as needed. For example, acrylonitrile, the vinyl cyanide compound may be one or more selected from the group consisting of methacrylonitrile, and ethacrylonitrile.

The vinyl cyanide compound may be included, for example, in an amount of 1 to 20% by weight, or 1 to 10% by weight based on the acrylic graft copolymer. Within this range, the yellowing of the resin composition is not exhibited and superior impact strength is exhibited.

The acrylic graft copolymer may be included, for example, in an amount of 10 to 50% by weight, 15 to 50% by weight, or 20 to 40% by weight based on the base resin. Within this range, superior impact strength and transparency are provided.

A refractive index difference between the copolymer, which includes the (meth)acrylic acid alkyl ester, the aromatic vinyl compound, and the vinyl cyanide compound, and the conjugated diene rubber may be, for example, less than ±0.01. The refractive index is used to provide transparency to the acrylic graft copolymer. The refractive index of the copolymer including the (meth)acrylic acid alkyl ester, the aromatic vinyl compound, and the vinyl cyanide compound, based on the refractive index of the conjugated diene rubber, absolutely affects transparency of the acrylic graft copolymer.

As another example, a difference between the refractive index of the copolymer including (meth)acrylic acid alkyl ester, an aromatic vinyl compound, and a vinyl cyanide compound and the refractive index of the conjugated diene rubber may be ±0.008 or less, or ±0.005 or less. Within this range, superior transparency is provided.

As a particular example, the refractive index of a polybutadiene rubber used in the example of the present invention is 1.518. In addition, the refractive indexes of monomers constituting the copolymer grafted with a conjugated diene rubber are as follows: methyl methacrylate: 1.49, acrylonitrile: 1.518, and styrene: 1.59. The refractive index of the copolymer including these monomers may be adjusted depending upon a mix ratio of the monomers. In addition, the refractive index of the copolymer may be calculated according to Equation 1 below.

Refractive index of graft copolymer=(Wt$A$×RI$A$)+ (Wt$S$×RI$S$)+(Wt$M$×RI$M$)     [Equation 1]

Wt$A$ represents % by weight of a vinyl cyanide compound, Wt$S$ represents % by weight of an aromatic vinyl compound, Wt$M$ represents % by weight of a (meth)acrylic acid alkyl ester compound, RI$A$ represents the refractive index of a vinyl cyanide compound, RI$S$ represents the refractive index of an aromatic vinyl compound, and RI$M$ represents the refractive index of a (meth)acrylic acid alkyl ester compound.

A method of polymerizing the acrylic graft copolymer is not specifically limited so long as an acrylic copolymer may be polymerized. Preferably, the acrylic graft copolymer may be polymerized through emulsion polymerization. More particularly, graft emulsion polymerization may be performed by adding the (meth)acrylic acid alkyl ester compound, the aromatic vinyl compound, and the vinyl cyanide compound to the conjugated diene rubber.

During the graft emulsion polymerization, a monomer may be added according to a method of adding the monomer batchwise or a method of continuously or sequentially a total or portion of the monomer. Preferably, the batch addition method and the continuous addition method may be used together. The polymerization may be performed, for example, at 60 to 85° C., or 70 to 85° C. for 1 to 8 hours, or 3 to 8 hours.

To perform the emulsion polymerization, for example, an emulsifier, a molecular weight regulator, and a polymerization initiator may be included.

The emulsifier is not specifically limited so long as it can be used in emulsion polymerization. As a particular example, the emulsifier may be one or more selected from the group consisting of commercially available alkyl aryl sulfonates, alkaline methyl alkyl sulfates, sulfonated alkyl ester, soaps of fatty acids, alkali salts of rosin acid, and reactive emulsifiers. The content of the emulsifier may be 0.1 to 3 parts by weight, or 0.2 to 1 parts by weight based on 100 parts by weight of the acrylic graft copolymer.

The molecular weight regulator is not specifically limited so long as it can be used in emulsion polymerization. As a particular example, the molecular weight regulator may be selected from mercaptans. Particularly, the molecular weight regulator may be tertiary dodecyl mercaptan. The content of the molecular weight regulator may be 0.1 to 2 parts by weight, or 0.2 to 1.5 parts by weight based on 100 parts by weight of the acrylic graft copolymer.

The polymerization initiator is not specifically limited so long as it can be used in emulsion polymerization. As a particular example, the polymerization initiator may be an oxidation-reduction catalyst based polymerization initiator, as a mixture of a peroxide, such as cumene hydroperoxide, diisopropylbenzene hydroperoxide, or persulfate, and a reductant, such as sodium formaldehyde sulfoxylate, sodium ethylenediamine tetraacetate, ferrous sulfate, dextrose, sodium pyrophosphate, or sodium sulfite. The content of the polymerization initiator may be 0.01 to 1 parts by weight, or 0.02 to 0.3 parts by weight based on 100 parts by weight of the acrylic graft copolymer.

The acrylic graft copolymer may be obtained, for example, in a latex form. The obtained latex may be collected as a dry powder through coagulation, dehydration, and drying processes.

The acrylic non-graft copolymer may be prepared, for example, by polymerizing a (meth)acrylic acid alkyl ester compound, an aromatic vinyl compound, and a vinyl cyanide compound.

The acrylic non-graft copolymer may be prepared, for example, by polymerizing 40 to 80% by weight of a (meth)acrylic acid alkyl ester compound, 10 to 40% by weight of an aromatic vinyl compound, and 1 to 20% by weight of a vinyl cyanide compound.

The (meth)acrylic acid alkyl ester compound may be, for example, one or more selected from the group consisting of (meth)acrylic acid methyl ester, (meth)acrylic acid ethyl ester, (meth)acrylic acid propyl ester, (meth)acrylic acid 2-ethylhexyl ester, (meth)acrylic acid decyl ester, and (meth)acrylic acid lauryl ester. The (meth)acrylic acid alkyl ester compound may be included in an amount of 40 to 80% by weight, 40 to 75% by weight, or 60 to 75% by weight with respect to the acrylic non-graft copolymer. Within this range, superior impact strength and transparency are provided.

The aromatic vinyl compound may be, for example, one or more selected from the group consisting of styrene, α-methyl styrene, p-methyl styrene, o-methyl styrene, p-ethyl styrene, and vinyl toluene. The aromatic vinyl compound may be included in an amount of 10 to 40% by weight, 15 to 40% by weight, or 15 to 30% by weight with respect to the acrylic non-graft copolymer. Within this range, superior mechanical properties and property balance are exhibited.

The vinyl cyanide compound may be, for example, one or more selected from the group consisting of acrylonitrile, methacrylonitrile, and ethacrylonitrile. The vinyl cyanide compound may be included in an amount of 1 to 20% by weight, 1 to 15% by weight, or 3 to 10% by weight with respect to the acrylic non-graft copolymer. Within this range, yellowing of a resultant resin composition does not occur and superior mechanical properties and transparency are provided.

The acrylic non-graft copolymer may have, for example, a weight average molecular weight of 80,000 to 300,000 g/mol, 80,000 to 200,000 g/mol, or 90,000 to 110,000 g/mol. Within this range, superior impact strength and superior processability due to excellent fluidity are exhibited.

A refractive index difference between the acrylic non-graft copolymer and the acrylic graft copolymer may be less than ±0.01. The refractive index is used to provide transparency to the thermoplastic resin composition. The refractive index of the acrylic non-graft copolymer, with respect to the refractive index of the acrylic graft copolymer, absolutely affects the transparency of the thermoplastic resin composition.

As another example, a difference between the refractive index of the acrylic non-graft copolymer and the refractive index of the acrylic graft copolymer may be ±0.008 or less, or ±0.005 or less. Within this range, superior transparency is exhibited. The refractive index of the acrylic non-graft copolymer may be calculated according to Equation 1 disclosed above.

The acrylic non-graft copolymer may be included, for example, in an amount of 50 to 90% by weight, 50 to 85% by weight, or 60 to 80% by weight based on the base resin. Within this range, superior impact strength and transparency are provided.

A method of polymerizing the acrylic non-graft copolymer is not specifically limited so long as an acrylic copolymer can be polymerized. For example, the acrylic non-graft copolymer may be polymerized through suspension polymerization or bulk polymerization. Preferably, the acrylic non-graft copolymer may be polymerized through continuous bulk polymerization. In this case, production costs may be reduced and thus economic feasibility is superior. In addition, in the case in which polymerization is performed in aqueous state as in emulsion polymerization, a vinyl cyanide compound, as a hydrophilic monomer, generates a large amount of homopolymer in aqueous state when the content of a vinyl cyanide compound is high, whereby a resultant resin is yellowed. On the other hand, in the case of bulk polymerization, generation of a homopolymer is small even when the content of a vinyl cyanide compound is considerably increased, whereby a yellowing degree is decreased and chemical resistance and impact resistance are improved.

During the polymerization, a polymerization conversion rate may be, for example, 60 to 90%, or 70 to 80%, and a total solid content (TSC) may be, for example, 50 to 70% by weight, or 55 to 65% by weight.

The zinc-based antimicrobial agent may be, for example, a zinc-supported inorganic support. As a particular example, the zinc-based antimicrobial agent may be zinc ions ($Zn^{2+}$)- supported inorganic support. The zinc ions ($Zn^{2+}$) impregnated in the inorganic support are slowly eluted to continuously function as an antimicrobial agent. When the zinc-based antimicrobial agent functions as an antimicrobial agent, a type of counter anions is not specifically limited.

A method of impregnating zinc ions ($Zn^{2+}$) in an inorganic support may be a general ion-exchange method. Here, the general ion-exchange method is not specifically limited so long as zinc ions may be impregnated.

The zinc-based antimicrobial agent may have, for example, an average particle diameter of greater than 3 μm to 30 μm, 5 to 20 μm, or 5 to 10 μm. Within this range, excellent transparency is exhibited, and superior initial antimicrobial activity and persistent antimicrobial activity are exhibited without property decrease.

A zinc content in the zinc-based antimicrobial agent may be, for example, 15 to 40% by weight, 20 to 35% by weight, or 20 to 30% by weight. Within this range, both initial antimicrobial activity and persistent antimicrobial activity are superior.

The inorganic support is not specifically limited so long as zinc ions can be impregnated therein and slowly eluted according to an ion-exchange method. For example, the inorganic support may be one or more selected from the group consisting of a glass-based support, zeolite, zircon, zirconium phosphate, calcium phosphate, and silica gel. Preferably, the inorganic support may be a glass-based support.

The glass-based support may be, for example, one or more selected from the group consisting of a glass powder, a glass bead, a hollow glass bead, a glass flake, and a glass fiber.

The zinc-based antimicrobial agent may be included, for example, in an amount of greater than 0.3 parts by weight and less than 1.2 parts by weight, 0.4 to 1.1 parts by weight, or 0.5 to 1 parts by weight based on 100 parts by weight of the base resin. Within this range, superior transparency and persistent antimicrobial activity are exhibited, and economic feasibility is superior in terms of production costs.

The thermoplastic resin composition may have, for example, a transparency (haze) of 10 or less, 1 to 10, or 5 to 10. Within this range, superior transparency is provided.

The thermoplastic resin composition may have, for example, an initial antimicrobial activity of 97% or more, 97 to 99.99%, or 99 to 99.99%.

The thermoplastic resin composition may have, for example, a persistent antimicrobial activity of 97% or more, 97 to 99.9%, or 99 to 99.9%.

The thermoplastic resin composition may be, for example, a transparent thermoplastic resin composition.

The thermoplastic resin composition may include one or more additives selected from the group consisting of a stabilizer, a pigment, a dye, a reinforcing agent, an ultraviolet absorber, an antioxidant, a coloring agent, a releasing agent, a lubricant, an antistatic agent, and a plasticizer according to a purpose within a range within which the properties of each ingredient are not damaged.

A molded article according to the present invention includes the thermoplastic resin composition.

The molded article may be, for example, an injection-molded article. As a particular example, the molded article may be a housing for household appliances such as air conditioners, vacuum cleaners, washing machines, refrigerators, and TV back covers; a housing for OA machines such as computers, notebooks, monitors, facsimiles, telephones, copiers, and scanners; an automotive component such as an automotive interior or exterior material; a member for toys; a leisure good; an upholstery; or the like.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

PREPARATION EXAMPLES

Preparation Example 1—Preparation of Acrylic Graft Copolymer (A)

100 parts by weight of ion exchanged water, 0.5 parts by weight of alkenyl C16-18 succinic acid dipotassium salt as a reactive emulsifier, 35 parts by weight of methyl methacrylate, 12 parts by weight of styrene, 3 parts by weight of acrylonitrile, 0.5 parts by weight of tertiary dodecyl mercaptan, 0.048 parts by weight of sodium formaldehyde sulfoxylate, 0.012 parts by weight of sodium ethylenediaminetetraacetate, 0.001 parts by weight of ferrous sulfate, and 0.04 parts by weight of cumene hydroperoxide were added to 50 parts by weight of a large-diameter polybutadiene rubber latex having an average particle diameter of 3,000 Å (based on a solid content, gel content: 86% by weight, swelling index: 15), which has been prepared through emulsion polymerization, at 75° C. over five hours, and reaction was allowed. After the reaction, temperature was elevated to 80° C. and then aging was performed for one hour, followed by terminating reaction. Here, a polymerization conversion rate was 98.8% and the amount of a solid coagulum was 0.1% by weight. Subsequently, solidification was performed using 3.5 parts by weight of an aqueous calcium chloride solution and washing and drying were performed. As a result, a powder-type acrylic graft copolymer was obtained.

Preparation Example 2—Preparation of Acrylic Non-Graft Copolymer (B)

A raw material mixture including 30 parts by weight of toluene, as a solvent, and 0.15 parts by weight of t-dodecyl mercaptan, as a molecular weight regulator, along with 70 parts by weight of methyl methacrylate, 25 parts by weight of styrene, and 5 parts by weight of acrylonitrile, was continuously fed into a reaction tank during an average reaction time of 4 hours, and a reaction temperature was maintained at 148° C. A polymerized solution discharged from the reaction tank was heated in a preheating tank, and an unreactive monomer in a volatilization tank was volatilized. Subsequently, a pellet-type acrylic non-graft copolymer was prepared at 210° C. by means of a polymer transfer pump extrusion machine. Here, a polymerization conversion rate was 70 to 80%, a total solid content (TSC) was 55 to 65% by weight, and a weight average molecular weight was 90,000 to 100,000 g/mol.

EXAMPLE

Examples 1 to 4 and Comparative Examples 1 to 7

An acrylic graft copolymer (A) prepared according to Preparation Example 1 and an acrylic non-graft copolymer (B-1) prepared according to Preparation Example 2 were mixed with an antimicrobial agent, i.e., a zinc-based antimicrobial agent (C-1) having an average particle diameter of 7 μm, an organic antimicrobial agent (C-2), a silver-based antimicrobial agent (C-3), or a zinc-based antimicrobial agent (C-4) having an average particle diameter of 3 μm in contents summarized in Table 1 below, and 0.3 parts by weight of a lubricant and 0.2 parts by weight of an antioxidant were added thereto. A pellet-type thermoplastic resin composition was prepared at a cylinder temperature of 220° C. by means of a twin-screw extrusion kneader. This resultant pellet-type thermoplastic resin composition was injection-molded, thereby manufacturing a specimen for measuring properties.

VZ601 (product name) manufactured by TOAGOSEI was used as the zinc-based antimicrobial agent (C-1) having an average particle diameter of 7 μm, ARSH DC (product name) manufactured by JS Green was used as the organic antimicrobial agent (C-2), IONPURE-wap (product name) manufactured by Ishizuka was used as the silver-based antimicrobial agent (C-3), and VZF200 (product name) manufactured by TOACOSEI was used as the zinc-based antimicrobial agent (C-4) having an average particle diameter of 3 μm.

TEST EXAMPLES

The properties of the acrylic resin composition specimen obtained according to each of Examples 1 to 4 and Comparative Examples 1 to 7 were measured according to the following methods. Results are summarized in Table 2 below.

Measurement Methods

Average particle diameter (Å) of conjugated diene rubber: Measured according to a dynamic laser light scattering method by means of a Nicomp 370HPL instrument manufactured by Nicomp, US.

Average particle diameter (μm) of antimicrobial agent: A d (0.5) value was measured by means of a particle diameter analyzer.

Gel content and swelling index: A polybutadiene rubber latex was solidified using a dilute acid or a metal salt, followed by washing. This washed polybutadiene rubber latex was dried for 24 hours in a 60° C. vacuum oven. An obtained rubber lump was cut into small pieces with scissors. Subsequently, 1 g of a rubber piece was placed in 100 g of toluene and stored for 48 hours in a dark room at room temperature, followed by separating into a sol and gel. The resultant sol and gel were respectively dried. Subsequently, a gel content was measured according to Equation 2 below and a swelling index was measured according to Equation 3 below:

$$\text{Gel content (\% by weight)} = \frac{\text{Weight of insoluble matter (gel)}}{\text{Weight of sample}} \times 100 \quad \text{[Equation 3]}$$

$$\text{Swelling index } (SI) = \frac{\text{Weight of swelled polymer gel}}{\text{Weight of dried polymer gel}}$$

Refractive index: A specimen was thinly spread to a thickness of about 0.2 mm, and then the refractive index thereof was measured at 25° C. by means of an Abbe's refractometer.

Weight average molecular weight (Mw, g/mol): Calibration was performed using the polymethylmethacrylate (PMMA) Standard through gel chromatography (GPC), and then a weight average molecular weight was measured.

Transparency (haze): Using a specimen, the haze value of a 3 mm sheet was measured according to a standard measurement method, ASTM D1003.

Melt index (g/10 min): The melt index of a specimen was measured according to a standard measurement method, ASTM D1238 (under conditions of 220° C. and 10 kg).

Impact strength (Notched Izod Impact Strength, kgfcm/cm): A ¼" specimen was used and the impact strength thereof was measured according to a standard measurement method, ASTM D256.

Initial antimicrobial activity (%): Using a specimen having a width of 5 cm×5 cm, different bacteria types, i.e., *Escherichia coli* and *Staphylococcus aureus*, were cultured under conditions of 37° C. and a relative humidity of 70 to 80% according to JIS Z 2801 (film adhesion method) and initial antimicrobial activity thereagainst was measurement.

Persistent antimicrobial activity (%): Under the Class 2 application condition (impregnating at 50° C. for 16 hours: lifespan warranty for 5 years or more) according to the Japanese SIAA standard, as an antimicrobial persistence evaluation standard, different bacteria types, i.e., *Escherichia coli* and *Staphylococcus aureus*, were cultured on a specimen with a width of 5 cm×5 cm under conditions of 37° C. and a relative humidity of 70 to 80% according to JIS Z 2801 (film adhesion method) and persistent antimicrobial activity thereof was measured.

TABLE 1

| Classification | Examples | | | | Comparative Examples | | | | | | |
|---|---|---|---|---|---|---|---|---|---|---|---|
| | 1 | 2 | 3 | 4 | 1 | 2 | 3 | 4 | 5 | 6 | 7 |
| A | 30 | 30 | 30 | 20 | 30 | 20 | 30 | 30 | 30 | 30 | 30 |
| B | 70 | 70 | 70 | 80 | 70 | 80 | 70 | 70 | 70 | 70 | 70 |
| C-1 | 0.5 | 0.7 | 1.0 | 0.5 | — | — | 0.3 | 1.2 | — | — | — |
| C-2 | — | — | — | — | — | — | — | — | 1.0 | — | — |
| C-3 | — | — | — | — | — | — | — | — | — | 1.0 | — |
| C-4 | — | — | — | — | — | — | — | — | — | — | 1.0 |
| * Properties | | | | | | | | | | | |
| Transparency | 7.0 | 8.1 | 10 | 6.8 | 2.0 | 1.8 | 5.1 | 14 | 2.1 | 20.5 | 80 |
| Melt index | 23.2 | 23.5 | 24.1 | 27.9 | 22.5 | 27.5 | 23.0 | 24.2 | 29.3 | 23 | 23 |
| Impact strength | 11 | 11 | 10.5 | 7 | 12 | 8 | 11 | 9 | 10 | 7 | 7 |

TABLE 1-continued

| Classification | Examples | | | | Comparative Examples | | | | | | |
| --- | --- | --- | --- | --- | --- | --- | --- | --- | --- | --- | --- |
| | 1 | 2 | 3 | 4 | 1 | 2 | 3 | 4 | 5 | 6 | 7 |
| Initial antimicrobial activity | 99.99 | 99.99 | 99.99 | 99.99 | 0 | 0 | 96.48 | 99.99 | 98.15 | 32.4 | 90.5 |
| Persistent antimicrobial activity | 99.9 | 99.9 | 99.9 | 99.9 | 0 | 0 | 96.1 | 99.9 | 35.2 | 44.1 | 89.1 |

As summarized in Table 1, it can be confirmed that, in the cases of Examples 1 and 4 according to the present invention, transparency and melt index are superior and both initial antimicrobial activity and persistent antimicrobial activity are 99.9% or more.

On the other hand, it can be confirmed that, in the cases of Comparative Examples 1 and 2 in which the antimicrobial agent was not included, both initial antimicrobial activity and persistent antimicrobial activity are not exhibited and, in the case of Comparative Example 3 in which a small amount of zinc-based antimicrobial agent is included, sufficient antimicrobial activity is not exhibited although initial antimicrobial activity and persistent antimicrobial activity are exhibited. In addition, it can be confirmed that, in the case of Comparative Example 4 in which the zinc-based antimicrobial agent is included in a large amount, transparency and impact strength are poor.

In addition, it can be confirmed that, in the case of Comparative Example 5 in which an organic antimicrobial agent is used instead of the zinc-based antimicrobial agent, persistent antimicrobial activity is very poor and, in the case of Comparative Example 6 in which a silver-based antimicrobial agent is used, both initial antimicrobial activity and persistent antimicrobial activity, as well as transparency and impact strength, are very poor. In addition, it can be confirmed that, in the case of Comparative Example 7 in which a zinc-based antimicrobial agent having a small average particle diameter is used, transparency is very poor, impact strength is decreased, and sufficient initial antimicrobial activity and persistent antimicrobial activity are not exhibited.

From these results, the present inventors confirmed that, when a zinc-based antimicrobial agent containing zinc with a particle diameter within a specific range is included, both initial antimicrobial activity and persistent antimicrobial activity are satisfied without property decrease, and thus, an existing expensive silver-based antimicrobial agent is not needed, whereby a thermoplastic resin composition superior with superior economic feasibility may be realized.

The invention claimed is:

1. A thermoplastic resin composition, comprising:
   100 parts by weight of a base resin that comprises an acrylic graft copolymer and an acrylic non-graft copolymer; and
   greater than or equal to 0.5 parts by weight and less than or equal to 1.0 parts by weight of a zinc-based antimicrobial agent,
   wherein the zinc-based antimicrobial agent has an average particle diameter of greater than 3 μm to 30 μm, and
   wherein the thermoplastic resin composition has an initial antimicrobial activity of 97% or more and has a persistent antimicrobial activity of 97% or more.

2. The thermoplastic resin composition according to claim 1, wherein the acrylic graft copolymer is prepared by graft-polymerizing a conjugated diene rubber with one or more selected from the group consisting of a (meth)acrylic acid alkyl ester compound, an aromatic vinyl compound, and a vinyl cyanide compound.

3. The thermoplastic resin composition according to claim 2, wherein the acrylic graft copolymer is prepared by polymerizing 10 to 60% by weight of a conjugated diene rubber, 30 to 70% by weight of a (meth)acrylic acid alkyl ester compound, 5 to 30% by weight of an aromatic vinyl compound, and 1 to 20% by weight of a vinyl cyanide compound.

4. The thermoplastic resin composition according to claim 2, wherein the conjugated diene rubber has an average particle diameter of 2,500 to 5,000 Å.

5. The thermoplastic resin composition according to claim 2, wherein a refractive index difference between the copolymer, which comprises the (meth)acrylic acid alkyl ester, the aromatic vinyl compound, and the vinyl cyanide compound, and the conjugated diene rubber is less than ±0.01.

6. The thermoplastic resin composition according to claim 1, wherein the acrylic non-graft copolymer is prepared by polymerizing a (meth)acrylic acid alkyl ester compound, an aromatic vinyl compound, and a vinyl cyanide compound.

7. The thermoplastic resin composition according to claim 6, wherein the acrylic non-graft copolymer is prepared by polymerizing 40 to 80% by weight of a (meth)acrylic acid alkyl ester compound, 10 to 40% by weight of an aromatic vinyl compound, and 1 to 20% by weight of a vinyl cyanide compound.

8. The thermoplastic resin composition according to claim 1, wherein the acrylic non-graft copolymer has a weight average molecular weight of 80,000 to 300,000 g/mol.

9. The thermoplastic resin composition according to claim 1, wherein a refractive index difference between the acrylic non-graft copolymer and the acrylic graft copolymer is less than ±0.01.

10. The thermoplastic resin composition according to claim 1, wherein the acrylic graft copolymer is comprised in an amount of 10 to 50% by weight and the acrylic non-graft copolymer is comprised in an amount of 50 to 90% by weight, based on 100 parts by weight of the base resin.

11. The thermoplastic resin composition according to claim 1, wherein the zinc-based antimicrobial agent is a zinc-supported inorganic support.

12. The thermoplastic resin composition according to claim 11, wherein the inorganic support is one or more selected from the group consisting of a glass-based support, zeolite, zircon, zirconium phosphate, calcium phosphate, and silica gel.

13. The thermoplastic resin composition according to claim 1, wherein a zinc content in the zinc-based antimicrobial agent is 15 to 40% by weight.

14. The thermoplastic resin composition according to claim 1, wherein the thermoplastic resin composition has a transparency (haze) of 10 or less.

15. The thermoplastic resin composition according to claim 1, wherein the thermoplastic resin composition is a transparent thermoplastic resin composition.

16. A molded article comprising the thermoplastic resin composition according to claim 1.

* * * * *